(12) United States Patent
Koshimizu

(10) Patent No.: US 9,063,048 B2
(45) Date of Patent: Jun. 23, 2015

(54) HARDNESS TESTER AND PROGRAM

(75) Inventor: Fumihiko Koshimizu, Zama (JP)

(73) Assignee: MITUTOYO CORPORATION, Kanagawa (JP)

( * ) Notice: Subject to any disclaimer, the term of this patent is extended or adjusted under 35 U.S.C. 154(b) by 281 days.

(21) Appl. No.: 13/547,687

(22) Filed: Jul. 12, 2012

(65) Prior Publication Data

US 2014/0013834 A1    Jan. 16, 2014

(51) Int. Cl.
*G01N 3/48*    (2006.01)
*G01N 3/42*    (2006.01)

(52) U.S. Cl.
CPC .......... *G01N 3/42* (2013.01); *G01N 2203/0208* (2013.01); *G01N 2203/0647* (2013.01)

(58) Field of Classification Search
CPC ... G01N 3/42; G01N 3/48; G01N 2203/0286; G01N 2203/0078
USPC ........................................................ 73/81, 82
See application file for complete search history.

(56) References Cited

U.S. PATENT DOCUMENTS

| | | | | |
|---|---|---|---|---|
| 4,147,052 | A * | 4/1979 | Tsujiuchi et al. | 73/81 |
| 4,463,600 | A * | 8/1984 | Hobbs et al. | 73/81 |
| 5,146,779 | A * | 9/1992 | Sugimoto et al. | 73/81 |
| 5,355,721 | A * | 10/1994 | Las Navas Garcia | 73/82 |
| 5,804,707 | A * | 9/1998 | Scarton et al. | 73/82 |
| 6,247,355 | B1 * | 6/2001 | Suresh et al. | 73/82 |
| 6,247,356 | B1 * | 6/2001 | Merck et al. | 73/82 |
| 6,279,388 | B1 * | 8/2001 | Tsujii et al. | 73/82 |
| 6,336,359 | B1 * | 1/2002 | Kawazoe et al. | 73/82 |
| 6,457,349 | B1 * | 10/2002 | Miyahara et al. | 73/82 |
| 6,842,267 | B1 * | 1/2005 | Morimatsu | 358/3.03 |
| 7,096,720 | B2 * | 8/2006 | Hayashi et al. | 73/81 |
| 7,121,136 | B2 * | 10/2006 | Tsujii et al. | 73/81 |
| 7,380,443 | B2 * | 6/2008 | Tsujii et al. | 73/81 |
| 2001/0033696 | A1 * | 10/2001 | Yokose | 382/238 |
| 2003/0070475 | A1 * | 4/2003 | Nagashima et al. | 73/81 |
| 2004/0096093 | A1 * | 5/2004 | Hauck et al. | 382/141 |

(Continued)

FOREIGN PATENT DOCUMENTS

| | | |
|---|---|---|
| JP | 7-181120 | 7/1995 |
| JP | 2005-326169 | 11/2005 |
| JP | 2011-164009 | 8/2011 |

OTHER PUBLICATIONS

U.S. Appl. No. 13/472,745 to Masaru Kawazoe, filed May 16, 2012.

(Continued)

*Primary Examiner* — Hezron E Williams
*Assistant Examiner* — Rodney T Frank
(74) *Attorney, Agent, or Firm* — Greenblum & Bernstein, P.L.C.

(57) ABSTRACT

A hardness tester having an image capturer capturing an indentation image, a data memory, an automatic size-scanning program scanning an indentation size, and a hardness calculation program includes: an identification information providing program providing image data with test specimen identification information and indentation identification information; a memory control program having the image data associated with the identification information stored; a specifying program specifying, when a scanning error occurs, identification information of image data in which the scanning error has occurred; an obtaining program obtaining the image data from the data memory based on the specified identification information; and a re-scanner (a display, an operator, and a manual size-calculation program) re-scanning an indentation size from the obtained image data.

3 Claims, 5 Drawing Sheets

(56) References Cited

U.S. PATENT DOCUMENTS

| | | |
|---|---|---|
| 2010/0191124 A1* | 7/2010 | Prokoski .................. 600/473 |
| 2012/0085154 A1 | 4/2012 | Takemura et al. |
| 2012/0087567 A1 | 4/2012 | Takemura et al. |
| 2012/0101743 A1 | 4/2012 | Sawa et al. |
| 2013/0319071 A1* | 12/2013 | Vodnick et al. ............. 73/1.08 |

OTHER PUBLICATIONS

U.S. Appl. No. 13/570,392 to Kozo Ariga, filed Aug. 9, 2012.

* cited by examiner

Fig. 3

| Capt. No. | Image Data | Test Specimen ID Info. | Indentation ID Info. | Indentation Size | Hardness (HV) | Error Yes/No |
|---|---|---|---|---|---|---|
| 1 | ◇ | 1/10 | A | | | |
| 2 | ◇ | 1/10 | B | | | |
| 3 | ◇ | 1/10 | C | | | |
| 4 | ◇ | 2/10 | A | | | |

H

HARDNESS TESTER AND PROGRAM

BACKGROUND OF THE INVENTION

1. Field of the Invention

The present invention relates to a hardness tester and a program.

2. Description of Related Art

Conventionally, a Vickers hardness tester is known in which hardness of a test specimen is evaluated based on an indentation formed by pressing an indenter loaded with a predetermined load against a surface of the test specimen. As such a Vickers hardness tester, a device has been developed which automatically performs positioning of a test specimen and automatically scans a Vickers indentation. For example, Japanese Patent Laid-open Publication No. H07-181120 proposes an automatic Vickers hardness scanning device that automatically measures Vickers hardness by generating, from an obtained image of an indentation, an indentation image from which influence due to scratches and dirt has been removed, and by calculating a surface area of the indentation. Further, Japanese Patent Laid-open Publication No. 2005-326169 proposes a device that is capable of securing a test area based on obtained surface image data of a test specimen. In other words, Japanese Patent Laid-open Publication No. 2005-326169 proposes a hardness tester capable of automatically selecting a region appropriate for a hardness test to perform a hardness test. The hardness testers in Japanese Patent Laid-open Publication Nos. H07-181120 and 2005-326169 employ technologies that enable prevention of scanning errors due to dirt and dusts on a surface of a test specimen and/or the shape of the test specimen. Even when these technologies are employed, however, a scanning error may occur for an indentation having an irregular surface pattern or being formed over a plurality of textures, for example. In such a case, an operation is performed to recover error data in which a scanning error has occurred.

In general, there are many occasions in which an operator is working on another operation while performing multi-point measurement with a hardness tester. Thus, it is likely that the operator is not observing statuses of all the tests. Therefore, the operator recognizes error data when reviewing a test result after completing all the measurement, and then performs an operation to recover the error data. Specifically, in a recovery operation with a device that successively tests a plurality of test specimens having the same shape, for example, an operator specifies a test specimen and an indentation at issue from the plurality of tested test specimens. Then, the operator carries out measurement again based on an observation on the indentation, or start over a process from formation of an indentation. As described above, conventional recovery operations require a great amount of work such as visually identifying an indentation in which an error has occurred, observing an indentation again to perform re-measurement, or starting over a process from formation of an indentation.

SUMMARY OF THE INVENTION

An advantage of the present invention is to make a recovery operation easier in a case where a scanning error occurs in a hardness tester that automatically measures Vickers hardness.

In order to achieve the advantage above, a hardness tester of the present invention has an image capturer capturing an image of an indentation after the indentation is formed by an indenter loaded with a predetermined load and pressed against a surface of a test specimen mounted on a test stage; a memory storing image data of the indentation image captured by the image capturer; an automatic size scanner scanning a size of the indentation from the image data stored in the memory; and a hardness calculator calculating hardness of the test specimen using the indentation size scanned by the automatic size scanner. The hardness scanner includes: an identification information provider providing the image data with test specimen identification information that identifies each test specimen and indentation identification information that identifies each indentation on a test specimen; a memory controller causing the memory to store the image data, and the test specimen identification information and the indentation identification information in association with the image data; a specifier specifying, when a scanning error is caused by the automatic size scanner, test specimen identification information and indentation identification information of image data in which the scanning error has occurred; an obtainer obtaining image data from the memory based on the test specimen identification information and the indentation identification information specified by the specifier; and a re-scanner re-scanning an indentation size from the image data obtained by the obtainer.

In the hardness tester according to another aspect of the present invention, the re-scanner includes a display displaying an image based on the image data obtained by the obtainer; a specifier with which a user specifies arbitrary points in the image displayed by the display; and a manual size calculator specifying coordinates of points specified by the specifier and calculating an indentation size based on the specified coordinates.

Another aspect the present invention is a program causing a computer to act as: an identification information provider providing an image data with test specimen identification information that identifies each test specimen and indentation identification information that identifies each indentation in the test specimen, the image data being obtained from an image of an indentation formed by an indenter loaded with a predetermined load and pressed against a surface of a test specimen mounted on a test stage; a memory controller causing the memory to store the image data, and the test specimen identification information and the indentation identification information in association with the image data; an automatic size scanner scanning an indentation size from the image data of the indentation image stored in the memory; a hardness calculator calculating hardness of the test specimen using the indentation size scanned by the automatic size scanner; a specifier specifying, when a scanning error is caused by the automatic size scanner, test specimen identification information and indentation identification information of image data in which the scanning error has occurred; an obtainer obtaining image data from the memory based on the test specimen identification information and the indentation identification information specified by the specifier; and a manual size calculator specifying, in a case where a user specifies arbitrary points on an image based on the image data obtained by the obtainer, coordinates of the specified points and calculating an indentation size from the specified coordinates.

According to the present invention, the hardness tester provides image data with test specimen identification information identifying each test specimen and indentation identification information identifying each indentation on the test specimen; stores, in a memory, the image data, and the test specimen identification information and the indentation identification information in association with the image data; and specifies, when a scanning error occurs, test specimen identification information and indentation identification information of image data in which the scanning error has occurred.

Then, based on the specified test specimen identification information and indentation identification information, the hardness tester obtains the image data from the memory, and re-scans a size of the indentation from the obtained image data. Accordingly, even when a scanning error occurs during measurement, it is possible to easily retrieve image data in which a scanning error has occurred and to perform re-scanning using the image data. Thereby, in a recovery operation, it is possible to eliminate work such as visually identifying a test specimen and an indentation at issue, starting over from formation of an indentation, and the like. Therefore, it is possible to improve usability of the hardness tester as well as work efficiency.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 3 is an example of a table stored in a memory;

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

Hereinafter, a hardness tester according to the present invention is descried in detail with reference to the drawings. A hardness tester 1 according to the present invention is an automatic hardness tester that captures an image of an indentation after the indentation is formed on a surface of a test specimen; automatically scans a size of the indentation from image data of the captured image of the indentation; and calculates hardness using the size. In a case where a scanning error occurs during automatic scanning of an indentation size, the hardness tester 1 is able to retrieve image data of the indention for which the scanning error has occurred and to re-scan the size of the indentation.

Figure 1:
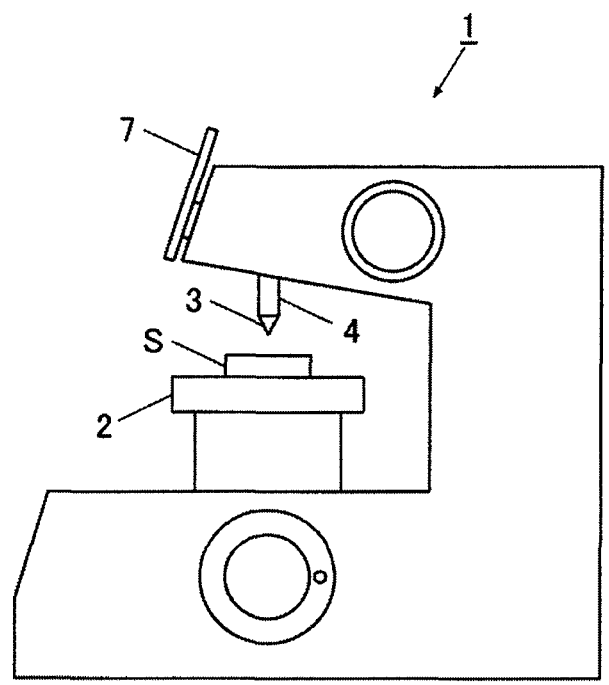
FIG. 1 is a schematic diagram illustrating a hardness tester of the present invention.
Figure 2:
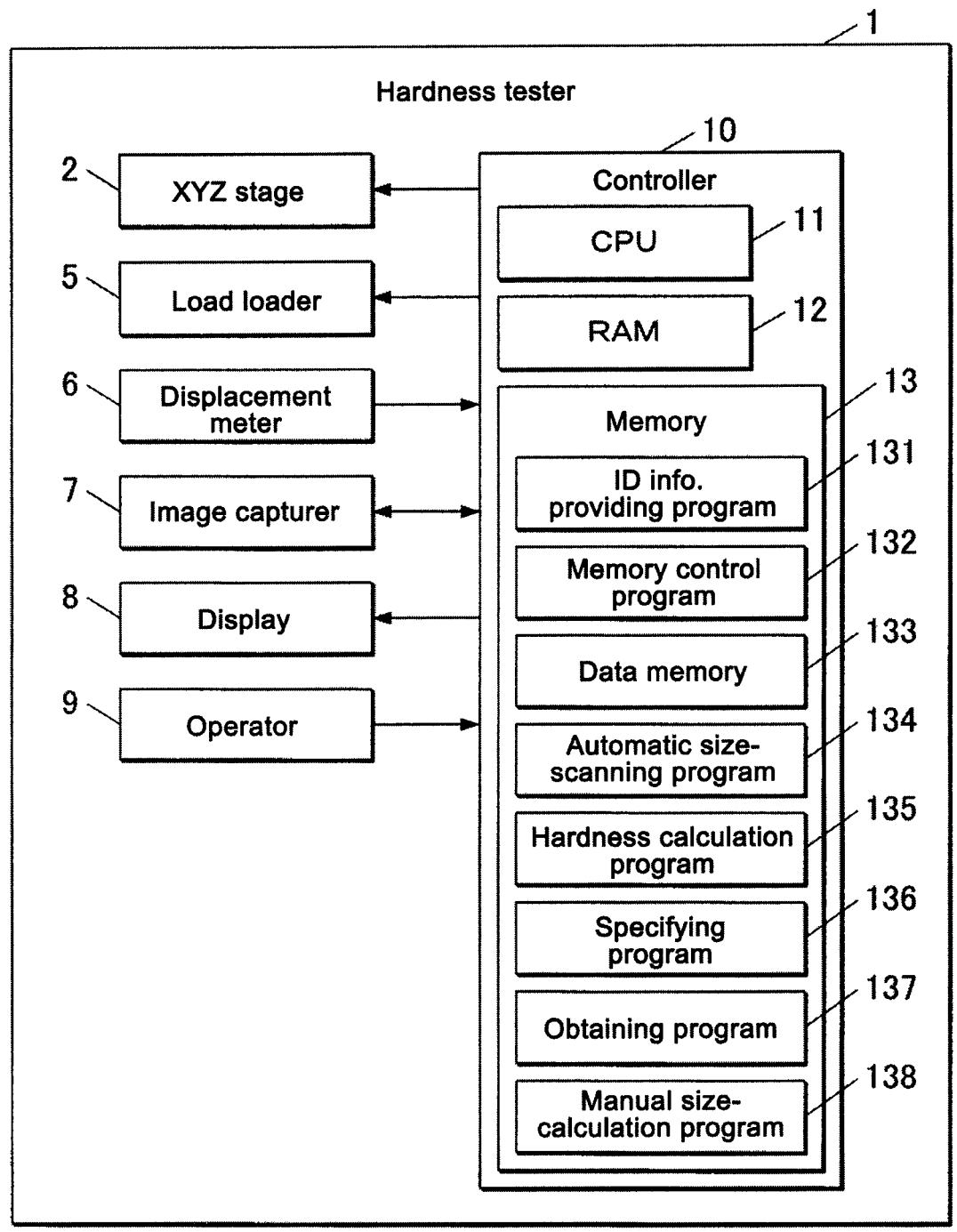
FIG. 2 is a block diagram illustrating a configuration to control the hardness tester in FIG. 1.

Specifically, as shown in FIGS. 1 and 2, the hardness tester 1 includes an XYZ stage 2, an indenter 3, an indenter shaft 4, a load loader 5, a displacement meter 6, an image capturer 7, a display 8, an operator 9, a controller 10, and the like.

The XYZ stage 2 is configured to move in X, Y, and Z directions (that is, horizontal and vertical directions) according to a control signal input from the controller 10. A test specimen S is moved back and forth, left and right, and up and down by the XYZ stage 2 so as to adjust a location relative to the indenter 3. In addition, the XYZ stage 2 holds the test specimen S such that the test specimen S mounted on an upper surface thereof is not displaced during test measurement.

As the indenter 3, a Vickers pyramid indenter (having a facing angle of 136±0.5°) made of diamond, for example, may be used. Such an indenter 3 forms an indentation on the surface of the test specimen S when loaded with a predetermined load and pressed against the surface of the test specimen S.

The indenter shaft 4 is provided with the indenter 3 at a distal end thereof. The load loader 5 is moved in an axial direction of the shaft by a drive force generated by a predetermined drive current supplied to a drive coil (not shown in the drawings) so as to press the indenter 3 against the surface of the test specimen S.

The load loader 5 includes the drive coil (not shown in the drawings) placed in a magnetic field, a power supply (not shown in the drawings) supplying a drive current to the drive coil, and the like, in order to load predetermined drive force (test force) to the indenter shaft 4. In the load loader 5, a predetermined test force is set based on an operation with the operator 9, and the drive current is then supplied to the drive coil so as to generate the set predetermined drive force (test force).

The displacement meter 6 measures how deep the indenter 3 is pushed in the test specimen S when the load loader 5 is loaded with a predetermined load. Specifically, the displacement meter 6 measures an amount of displacement of the indenter 3 when the indenter 3 loaded with a predetermined load is pressed against the surface of the test specimen S and forms an indentation on the surface of the test specimen S. As the displacement meter 6, a capacitive displacement sensor, for example, may be used, the capacitive displacement sensor detecting how deep the indenter 3 is pushed in based on a difference in capacitance.

The image capturer 7 includes a camera and the like, for example, and captures, on the XYZ stage 2, for example, an image of an indentation or the like formed on the surface of the test specimen S by the indenter 3, according to a control signal input from the controller 10.

The display 8 is a liquid crystal display panel, for example, and performs processing to display various images, a test result, and the like, according to a control signal input from the controller 10. Specifically, the display 8 displays a surface image of the test specimen S captured by the image capturer 7. In addition, the display 8 displays an image based on image data having a scanning error and obtained by execution of an obtaining program 137 described later.

The operator 9 is a group of operation keys such as a keyboard and the like, for example. When the operator 9 is operated by a user, the operator 9 outputs an operation signal associated with the operation to the controller 10. Further, the operator 9 may also include other operation devices: a pointing device such as a mouse, a remote controller, and the like. The operator 9 is operated by a user when inputting directions for performing a hardness test with respect to the test specimen S, when setting measurement conditions (test force (that is, a load) applied to the indenter 3, the number of indentations to be formed on one test specimen, and the like), when setting a position where an indentation is formed on a test specimen, and the like. In addition, the operator 9 is also operated, as a specifier, to specify arbitrary points on an image when the image based on image data having a scanning error is displayed on the display 8. Further, the operator 9 may be configured with a touch panel provided so as to cover a screen of the display 8. When detecting a user's touch operation, such a touch panel generates a detection signal indicating coordinates of a relative position of an operation position and outputs the signal to the controller 10.

The controller 10 is configured with a CPU (Central Processing Unit) 11, a RAM (Random Access Memory) 12, a memory 13, and the like. The controller 10 is connected to the XYZ stage 2, the load loader 5, the displacement meter 6, the image capturer 7, the display 8, the operator 9, and the like, via a system bus and the like.

The CPU 11 performs various control processing, for example, according to various processing programs for the hardness tester stored in the memory 13.

The RAM 12 includes, for example, a program storage area for deploying a processing program and the like executed by the CPU 11; a data storage area storing input data, a processing result, and the like generated when a processing program is executed; and the like.

The memory 13 stores, for example, a system program executable on the hardness tester 1; various processing programs executable under the system program; data used when the various processing programs are executed; data of various processing results arithmetically processed by the CPU 11; and the like. A program is stored in the memory 13 in the form of computer readable program codes.

Specifically, the memory 13 stores, for example, an identification information providing program 131, a memory control program 132, a data memory 133, an automatic size-scanning program 134, a hardness calculation program 135, a specifying program 136, the obtaining program 137, a size-calculation program 138, and the like.

The identification information providing program 131 is a program, for example, that causes the CPU 11 to provide image data with test specimen identification information that identifies each test specimen and indentation identification information that identifies each indentation on a test specimen. Specifically, the CPU 11 executes the identification information providing program 131 when an image of an indentation is captured by the image capturer 7, and provides image data of the captured image with test specimen identification information and indentation identification information. Test specimen identification information is information to identify each test specimen and uses a symbol such as a number, an alphabet, and the like. For example, when measurement is performed on 10 test specimens, the test specimens are sequentially provided from the first test specimen with information such as "1/10, 2/10, 3/10, . . . 10/10", "1, 2, 3, . . . , 10", "A, B, C, . . . , J", or the like as test specimen identification information. Indentation identification information is information to identify each indentation on each test specimen, and uses a symbol such as a number, an alphabet, and the like. For example, when three indentations are formed on one test specimen, information such as "A, B, and C", "1, 2, and 3", or the like is provided as indentation identification information to each test specimen in the order of formation. Further, as indentation identification information, coordinate information may be used that indicates a position of an indentation formed on a test specimen. In such a case, when three indentations are formed on one test specimen, for example, coordinate information such as A(X1,Y1), B(X2,Y2), C(X3, Y3) and the like are provided to indentations, respectively, as indentation identification information. The CPU 11 acts as an identification information provider by executing the identification information providing program 131.

The memory control program 132 is a program, for example, that causes the CPU 11 to store, in the data memory 133, image data, and test specimen identification information and indentation identification information in a manner associated with the image data. Specifically, when test specimen identification information and indentation identification information is provided to image data by execution of the identification information providing program 131, the CPU 11 executes the memory control program 132. Thereby, as shown in FIG. 3, the CPU 11 stores, in the data memory 133, the image data, and the test specimen identification information and the indentation identification information in a manner associated with the image data. The CPU 11 acts as a memory controller by executing the memory control program 132.

The data memory 133 stores, as a data memory, image data of an indentation image captured by the image capturer 7, and the like. Each image data is stored in a manner associated with test specimen identification information and indentation identification information.

FIG. 3 shows an example of a table T that is stored in the data memory 133. The table T includes the following items: "Capturing No.", "Image Data", "Test Specimen Identification Information", "Indentation Identification Information", "Indentation Size", "Hardness (HV)", and "Error Yes/No". "Capturing No." is a number indicating the order of image capturing performed in one sequential measurement. "Image Data" is image data of a captured indentation. "Test Specimen Identification Information" is identification information indicating the order of test specimens measured in one sequential measurement. FIG. 3 shows an example in which 10 test specimens are measured and are sequentially provided with information 1/10, 2/10, . . . , and 10/10, respectively, from the first specimen. "Indentation Identification Information" is identification information indicating each indentation on one test specimen. FIG. 3 shows an example in which three indentations are formed on one test specimen and are sequentially provided with information A, B, and C, respectively, from the indentation formed first. "Indentation Size" is a value of an indentation size obtained by execution of the automatic size-scanning program 134 described later. "Hardness (HV)" is a value of hardness obtained by execution of the hardness calculation program 135 described later. "Error Yes/No" is information which is "Yes" or "No" given by execution of the specifying program 136 described later.

Accordingly, for example, the first line in FIG. 3 illustrates image data obtained through a first image capturing, the image data obtained from an indentation A on a first test specimen among the 10 test specimens. The second line in FIG. 3 illustrates image data obtained through a second image capturing, the image data obtained from an indentation formed in a position B on the first test specimen among the 10 test specimens. The third line in FIG. 3 illustrates image data obtained through a third image capturing, the image data obtained from an indentation formed in a position C on the first test specimen among the 10 test specimens. The fourth line in FIG. 3 illustrates image data obtained through a fourth image capturing, the image data obtained from an indentation formed in a position A on the second test specimen among the 10 test specimens.

The automatic size-scanning program 134 is a program that causes the CPU 11 to scan an indentation size from the image data stored in the data memory 133. Specifically, the CPU 11 digitizes indentation image data to have multivalued tones and detects a threshold value appropriate for the multivalued digital image of the indentation. Then, the CPU 11 obtains a binary image using the threshold value and selectively reduces influence of scratches and dirt by performing two-dimensional noise removal processing with respect to the binary image. Next, the CPU 11 detects approximate positions of four sides of the indentation in a screen. The CPU 11 detects indentation border points based on the approximate positions and obtains four polynomial regression curves from the border points. While estimating intersections of these four polynomial regression curves as vertexes of the indentation, the CPU 11 calculates lengths (size of indentation) of mutually intersecting two diagonal lines from coordinate positions of the four vertexes. The value of the calculated indentation size is stored in "Indentation Size" of the table T in the data memory 133. The CPU 11 acts as an automatic size scanner by execution of the automatic size-scanning program 134.

The hardness calculation program 135 is a program that causes the CPU 11 to calculate hardness of a test specimen using indentation size scanned by execution of the automatic size-scanning program 134. Specifically, the CPU 11 calculates an indentation area (A) by arithmetically processing the indentation size (lengths of mutually interesting two diagonal lines) obtained by execution of the automatic size-scanning program 134. Next, test force (F) loaded at the time of formation of the indentation is divided by the calculated indentation area (A) in order to obtain hardness (HV). Specifically, hardness (HV) is calculated with the following formula (1).

$$HV=F/A \quad (1)$$

The calculated hardness (HV) value is stored in "Hardness (HV)" in the table T in the data memory 133. The CPU 11 acts as a hardness calculator by executing the hardness calculation program 135.

The specifying program 136 is a program that causes the CPU 11 to specify, when a scanning error occurs during execution of the automatic size-scanning program 134, test specimen identification information and indentation identification information of image data in which the scanning error has occurred. Specifically, when a scanning error occurs during execution of the automatic size-scanning program 134, the CPU 11 executes the specifying program 136, inputs "Yes" in the item "Error Yes/No" in the table T stored in the data memory 133, and specifies test specimen identification information and indentation identification information of image data in which the scanning error has occurred. Further, for image data having no scanning error, the item "Error Yes/No" in the table T becomes "No". The CPU 11 acts as a specifier by executing the specifying program 136.

The obtaining program 137 is a program that causes the CPU 11 to obtain image data from the data memory 133 based on the test specimen identification information and indentation identification information specified by executing the specifying program 136. Specifically, in a recovery operation, when a user operates the operator 9 to retrieve error data, the CPU 11 executes the obtaining program 137 to detect test specimen identification information and indentation identification information for which the entry of the item "Error Yes/No" in the table T is "Yes". The CPU 11 obtains image data corresponding to the information from the data memory 133 and displays the image data on the display 8. The CPU 11 acts as an obtainer by executing the obtaining program 137.

The size-calculation program 138 is a program that causes the CPU 11 to specify, when a user specifies arbitrary points on an image based on the image data obtained by executing the obtaining program 137, coordinates of the specified points and to calculate an indentation size from the specified coordinates. Herein, the image displayed on the display 8 by execution of the obtaining program 137 is configured so as to allow a user to specify arbitrary points with the operator 9. Examples of the specifying method in this case includes a method in which a user operates keys of the operator 9 to move a cursor on a screen for confirmation, a method in which a touch panel is touch-operated, and the like. In a case where arbitrary four points are specified by a user on such an image, the CPU 11 executes the size-calculation program 138 to specify coordinates (X,Y) for each point, and calculates an indentation size (lengths of mutually intersecting two diagonal lines) using the value of the coordinates. Specifically, an indentation size is calculated by use of specified points. The CPU 11 acts as a size calculator by executing the size-calculation program 138.

When an indentation size is calculated by execution of the size-calculation program 138, the CPU 11 executes the hardness calculation program 135 described above and calculates hardness of a test specimen using the calculated indentation size. A user uses a hardness value of the test specimen calculated in this way and performs edit processing such as replacing corresponding data in the data memory 133. In the present embodiment, a re-scanner is configured with the display 8, the operator 9, and the size-calculation program 138.

Figure 4:
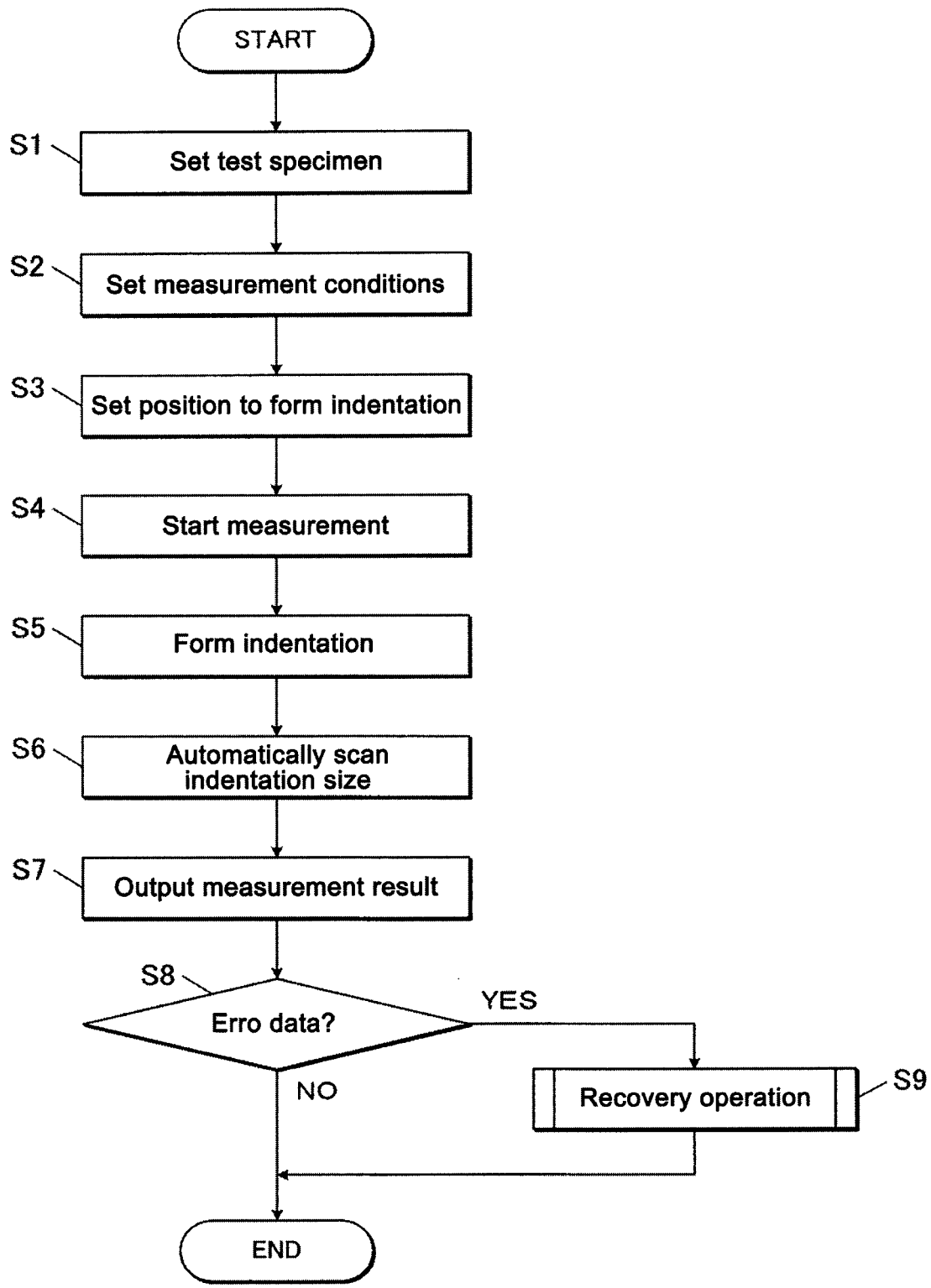
FIG. 4 is a flowchart describing an operation of the hardness tester in FIG. 1.

Next, operation of the hardness tester 1 is described using FIG. 4.

When a processing is started, first, in step S1, a user sets a test specimen. Next, in step S2, the user sets measurement conditions, and in subsequent step S3, the user sets a position to form an indentation. Next, in step S4, the CPU 11 starts measurement, and in subsequent step S5, the CPU 11 performs indentation formation for a predetermined number of times with respect to the set test specimen. Next, in step S6, the CPU 11 performs automatic scanning of an indentation size. In a case where a scanning error occurs at this point, the CPU 11 inputs "Yes" in the item "Error Yes/No" in the table T. Next, in step S7, the CPU 11 outputs a measurement result. Next, in step S8, the user determines whether or not there is any error data by referring to the output measurement result. In a case where no error data has been formed (step S8: No), the processing is completed. On the other hand, in a case where error data has been formed (step S8: Yes), the user completes the processing after performing a recovery operation (described later) in subsequent step S9.

Figure 5:
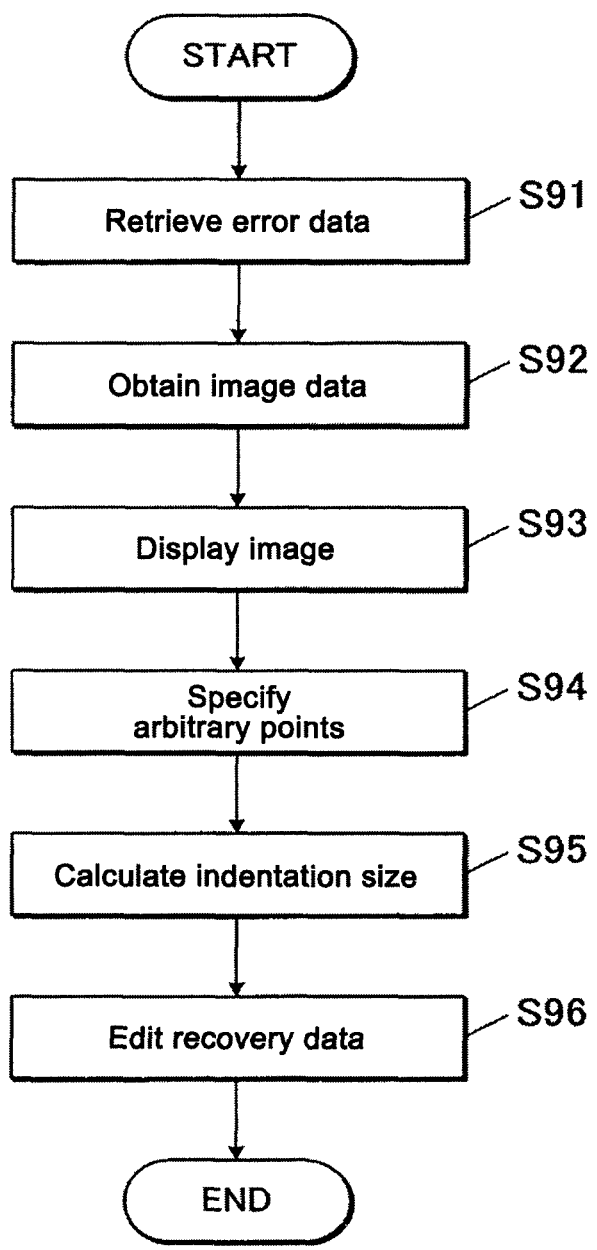
FIG. 5 is a flowchart describing an operation of a recovery operation.

The recovery operation in step S9 is described in the following using FIG. 5. First, in step S91, the user retrieves error data. Next, in step S92, the CPU 11 obtains image data from the data memory 133 based on "Yes" in "Error Yes/No" in the table T in the data memory 133. Next, in step S93, the CPU 11 displays an image on the display 8 based on the obtained image data. Next, in step S94, the user specifies arbitrary points in the displayed image. Next, in step S95, the CPU 11 specifies coordinates of the specified points and calculates an indentation size (that is, re-scans an indentation size) from the specified coordinates. Next, in step S96, the CPU 11 edits recovered data and completes the processing.

As described above, the hardness tester 1 according to the present embodiment provides image data with test specimen identification information and indentation identification information; stores the image data, and the test specimen identification information and the indentation identification information in a manner associated with the image data in the data memory 133; and specifies, in a case where a scanning error occurs, test specimen identification information and indentation identification information of image data in which the scanning error has occurred. Then, based on the specified test specimen identification information and indentation identification information, the hardness tester 1 obtains the image data from the data memory 133 and re-scans an indentation size from the obtained image data. Accordingly, even when a scanning error occurs during measurement, it is possible to easily retrieve image data of an indentation for which a scanning error has occurred and to perform re-scanning using the image data. Thus, in a recovery operation, it is possible to reduce work such as visually specifying a test specimen and an indentation at issue, starting over a process from formation of an indentation, and the like. In addition, when determining a cause of a scanning error, because of easiness of retrieving image data of an indentation for which a scanning error has occurred, a state of indentation can be easily observed, thereby improving convenience in use. Therefore, it is possible to improve usability of a hardness tester as well as work efficiency.

According to the hardness tester 1 of the present embodiment, a scanner is configured with the display 8, the operator 9, and the size-calculation program 138. The display 8 displays an image based on obtained image data. The operator 9 is used by a user to specify arbitrary points on an image displayed on the display 8. The size-calculation program 138 specifies coordinates of the points specified by the operator 9, and calculates an indentation size from the specified coordinates. Therefore, re-testing can be performed by merely retrieving the image in which the scanning error has occurred and specifying arbitrary points on the image, thereby enabling a series of recovery operation to be performed for a short period of time. In addition, stored image data can be used even after rebooting the hardness tester 1, which enhances usability. Moreover, stored image data can be retrieved by another tester in a case where the tester is configured in the same manner as a tester used for measurement, which enhances usability.

In the above embodiment, as a re-scanner, descriptions are provided with a configuration, as an example, in which a user specifies arbitrary points in an image displayed on the display 8 and an indentation size is calculated from coordinates of the arbitrary points, that is, a configuration in which an indentation size is manually specified. However, the re-scanner may be configured to perform automatic re-scanning after performing further image processing such as noise removal processing with respect to an image in which a scanning error has occurred.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester comprising:
    an image capturer configured to capture an image of an indentation after the indentation is formed by an indenter loaded with a predetermined load and pressed against a surface of a test specimen mounted on a test stage;
    a memory configured to store image data of the indentation image captured by the image capturer;
    an automatic size scanner configured to scan a size of the indentation from the image data stored in the memory;
    a hardness calculator configured to calculate hardness of the test specimen using the indentation size scanned by the automatic size scanner;
    an identification information provider configured to provide the image data with test specimen identification information which identifies each test specimen and indentation identification information which identifies each indentation on the test specimen;
    a memory controller configured to control the memory to store the image data and the test specimen identification information and the indentation identification information in association with the image data;
    a specifier configured to specify, when a scanning error occurs during scanning by the automatic size scanner, test specimen identification information and indentation identification information of image data in which the scanning error has occurred;
    an obtainer configured to obtain image data from the memory based on the test specimen identification information and the indentation identification information specified by the specifier; and
    a re-scanner configured to re-scan an indentation size from the image data obtained by the obtainer.

2. The hardness tester according to claim 1, wherein the re-scanner comprises:
    a display configured to display an image based on the image data obtained by the obtainer;
    a display specifier with which a user specifies points in the image displayed by the display; and
    a size calculator identifying coordinates of points specified by the display specifier and calculating an indentation size based on the identified coordinates.

3. At least one non-transitory computer readable medium that stores a set of executable instructions which, when executed by a processor, causes a computer to act as:
    an identification information provider configured to provide an image data with test specimen identification information that identifies each test specimen and indentation identification information that identifies each indentation on the test specimen, the image data being obtained from an image of an indentation formed by an indenter loaded with a predetermined load and pressed against a surface of a test specimen mounted on a test stage;
    a memory controller configured to control a memory to store the image data, and the test specimen identification information and the indentation identification information in association with the image data;
    an automatic size scanner configured to scan an indentation size from the image data of the indentation image stored in the memory;
    a hardness calculator configured to calculate hardness of the test specimen using the indentation size scanned by the automatic size scanner;
    a specifier configured to specify, when a scanning error occurs during scanning by the automatic size scanner, test specimen identification information and indentation identification information of image data in which the scanning error has occurred;
    an obtainer configured to obtain image data from the memory based on the test specimen identification information and the indentation identification information specified by the specifier; and
    a size calculator configured to identify, in a case where a user specifies points on an image based on the image data obtained by the obtainer, coordinates of the identified points and calculating an indentation size from the specified coordinates.

\* \* \* \* \*